(12) United States Patent
Sato et al.

(10) Patent No.: US 11,636,392 B2
(45) Date of Patent: Apr. 25, 2023

(54) INFORMATION PROCESSING DEVICE AND NON-TRANSITORY COMPUTER READABLE MEDIUM

(71) Applicant: Agama-X Co., Ltd., Tokyo (JP)

(72) Inventors: Masahiro Sato, Tokyo (JP); Kengo Tokuchi, Tokyo (JP)

(73) Assignee: Agama-X Co., Ltd., Tokyo (JP)

( * ) Notice: Subject to any disclaimer, the term of this patent is extended or adjusted under 35 U.S.C. 154(b) by 385 days.

(21) Appl. No.: 16/839,792

(22) Filed: Apr. 3, 2020

(65) Prior Publication Data

US 2021/0174251 A1 Jun. 10, 2021

(30) Foreign Application Priority Data

Dec. 5, 2019 (JP) .............................. JP2019-220278

(51) Int. Cl.
*G06N 20/00* (2019.01)
*G16H 40/67* (2018.01)
*A61B 5/369* (2021.01)

(52) U.S. Cl.
CPC ............. *G06N 20/00* (2019.01); *A61B 5/369* (2021.01); *G16H 40/67* (2018.01)

(58) Field of Classification Search
CPC ........ G06N 20/00; A61B 5/369; A61B 5/742; A61B 5/01; A61B 5/7264; A61B 5/7465; A61B 5/7475; A61B 2560/0487; A61B 5/02055; A61B 5/372; G16H 40/67; G06F 3/015; G06F 3/011
See application file for complete search history.

(56) References Cited

U.S. PATENT DOCUMENTS

| | | | |
|---|---|---|---|
| 2015/0338917 A1* | 11/2015 | Steiner | H04L 9/3271 345/156 |
| 2018/0113673 A1* | 4/2018 | Sheynblat | G10L 17/00 |
| 2019/0058703 A1* | 2/2019 | Zhu | A61B 5/374 |
| 2019/0204916 A1* | 7/2019 | Li | G06F 3/04847 |
| 2019/0384392 A1* | 12/2019 | Aimone | A61B 5/163 |
| 2020/0371515 A1* | 11/2020 | Westbrook | G06F 3/015 |

FOREIGN PATENT DOCUMENTS

JP 2015-211705 A 11/2015
JP 2016-67922 A 5/2016

\* cited by examiner

*Primary Examiner* — Stella L. Woo
(74) *Attorney, Agent, or Firm* — Hoffman Warnick LLC

(57) ABSTRACT

An information processing device includes a processor configured to query a user about an operation item to be executed by equipment in a case where biological information about the user satisfying a specific condition is acquired, but a single operation item of the equipment to associate with the acquired biological information is not specified, and associate an operation item designated by the user in response to the query with the acquired biological information.

14 Claims, 5 Drawing Sheets

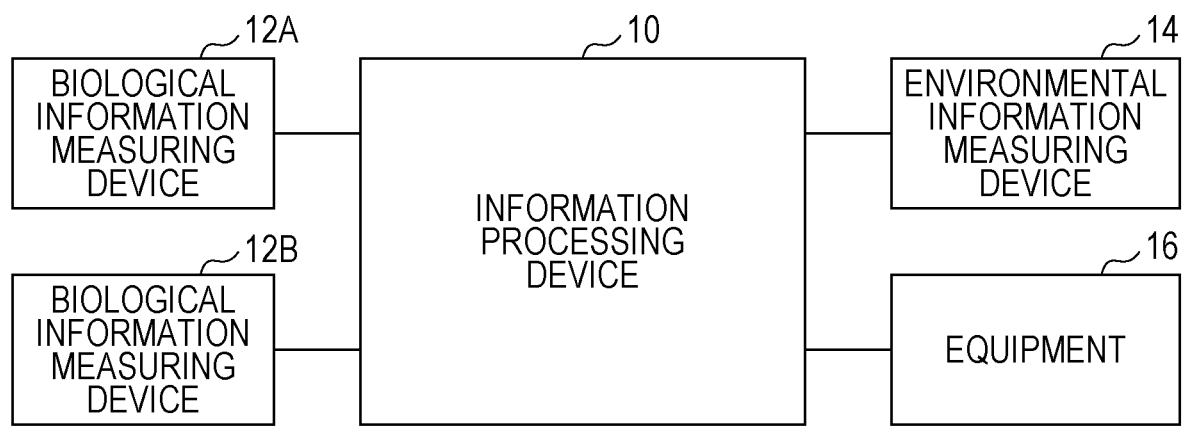
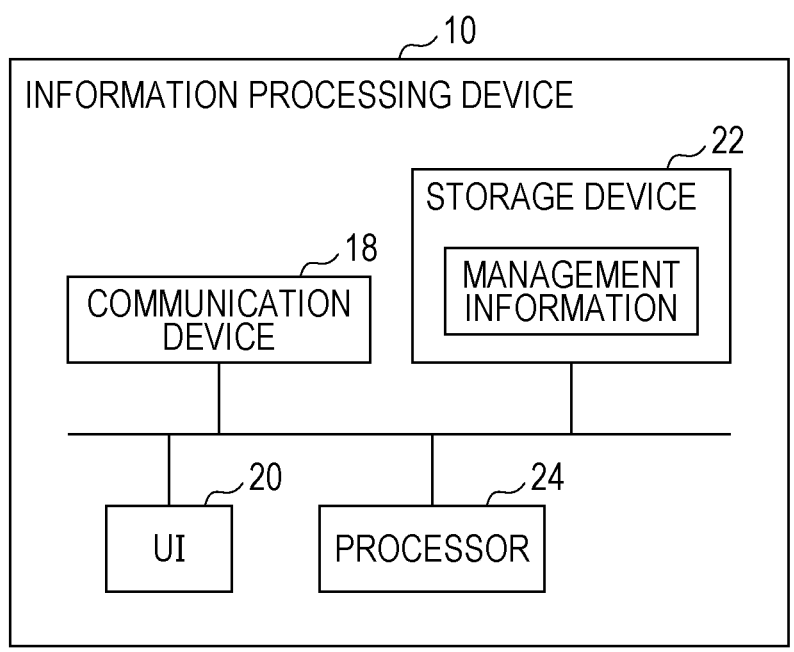

FIG. 4
| ID | STANDARD BRAIN WAVE | OPERATION INFORMATION |
|---|---|---|
| 1 |  | TURN ON COOLER OF AIR CONDITIONER |
| 2 |  | TURN OFF COOLER OF AIR CONDITIONER |
| ... | ... | ... |
FIG. 5
| ID | STANDARD BRAIN WAVE | OPERATION INFORMATION | USER INFORMATION |
|---|---|---|---|
| 1 |  | TURN ON COOLER OF AIR CONDITIONER | USER A |
| 2 |  | TURN ON COOLER OF AIR CONDITIONER | USER B |
| 3 |  | TURN OFF COOLER OF AIR CONDITIONER | USER A |
| ... | ... | ... | ... |

| ID | STANDARD BRAIN WAVE | OPERATION INFORMATION | USER INFORMATION |
|---|---|---|---|
| 1 | ～ | TURN ON COOLER OF AIR CONDITIONER | USER A |
| 2 | ～ | TURN ON COOLER OF AIR CONDITIONER | USER B |
| 3 | ～ | TURN OFF COOLER OF AIR CONDITIONER | USER A |
| 4 | ～ | TURN OFF COOLER OF AIR CONDITIONER | USER A |
| ... | ... | ... | ... |

FIG. 8

| ID | STANDARD BRAIN WAVE | STANDARD BODY TEMPERATURE | OPERATION INFORMATION | USER INFORMATION |
|---|---|---|---|---|
| 1 | ∿ | THRESHOLD OR GREATER | TURN ON COOLER OF AIR CONDITIONER | USER A |
| 2 | ∿ | THRESHOLD OR GREATER | TURN ON COOLER OF AIR CONDITIONER | USER B |
| 3 | ∿ | LESS THAN THRESHOLD | TURN OFF COOLER OF AIR CONDITIONER | USER A |
| 4 | ∿ | LESS THAN THRESHOLD | TURN OFF COOLER OF AIR CONDITIONER | USER A |
| ... | ... | ... | ... | ... |

FIG. 9

| ID | STANDARD BRAIN WAVE | STANDARD ENVIRONMENTAL INFORMATION | OPERATION INFORMATION | USER INFORMATION |
|---|---|---|---|---|
| 1 | ∿ | ROOM TEMPERATURE: 28°C OR GREATER | TURN ON COOLER OF AIR CONDITIONER | USER A |
| 2 | ∿ | ROOM TEMPERATURE: 28°C OR GREATER | TURN ON COOLER OF AIR CONDITIONER | USER B |
| 3 | ∿ | ROOM TEMPERATURE: LESS THAN 28°C | TURN OFF COOLER OF AIR CONDITIONER | USER A |
| 4 | ∿ | ROOM TEMPERATURE: LESS THAN 28°C | TURN OFF COOLER OF AIR CONDITIONER | USER A |
| ... | ... | ... | ... | ... |

INFORMATION PROCESSING DEVICE AND NON-TRANSITORY COMPUTER READABLE MEDIUM

CROSS-REFERENCE TO RELATED APPLICATIONS

This application is based on and claims priority under 35 USC 119 from Japanese Patent Application No. 2019-220278 filed Dec. 5, 2019.

BACKGROUND

(i) Technical Field

The present disclosure relates to an information processing device and a non-transitory computer readable medium.

(ii) Related Art

It is conceivable to operate equipment by using biological information such as brain waves.

Japanese Unexamined Patent Application Publication No. 2015-211705 describes a device that detects a brain-wave biological signal from the brain waves of a user, detects a surface electromyography biological signal from the surface myoelectric potential of the user, and computes a control signal on the basis of both biological signals.

Japanese Unexamined Patent Application Publication No. 2016-67922 describes a device that acquires the brain waves of the user and selectively operates multiple devices to be operated in accordance with an analysis result obtained by analyzing the brain waves.

SUMMARY

However, equipment may not necessarily be operated precisely using biological information.

Aspects of non-limiting embodiments of the present disclosure relate to applying an instruction for operating equipment intended by the user in a case of operating the equipment by using biological information about the user.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an information processing device including a processor configured to query a user about an operation item to be executed by equipment in a case where biological information about the user satisfying a specific condition is acquired, but a single operation item of the equipment to associate with the acquired biological information is not specified, and associate an operation item designated by the user in response to the query with the acquired biological information.

BRIEF DESCRIPTION OF THE DRAWINGS

An exemplary embodiment of the present disclosure will be described in detail based on the following figures, wherein:

FIG. 1 is a block diagram illustrating a configuration of an information processing system according to an exemplary embodiment;

FIG. 2 is a block diagram illustrating a configuration of an information processing device according to the exemplary embodiment;

FIG. 4 is a diagram illustrating a management table;

FIG. 5 is a diagram illustrating a management table;

FIG. 8 is a diagram illustrating a management table; and

FIG. 9 is a diagram illustrating a management table.

DETAILED DESCRIPTION

Figure 3:
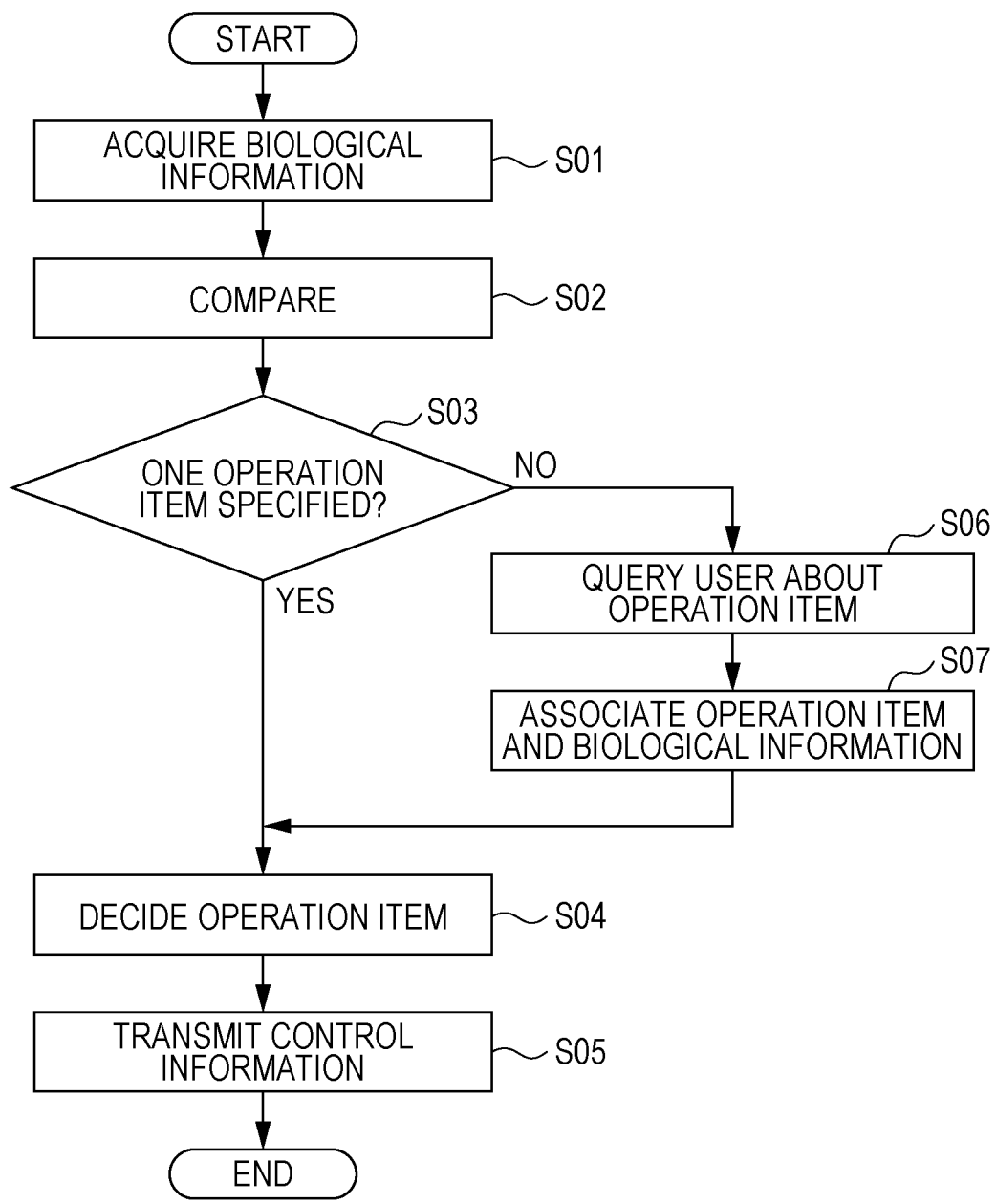
FIG. 3 is a diagram illustrating a flowchart that illustrates processes by the information processing device according to the exemplary embodiment.

An information processing system according to the exemplary embodiment will be described with reference to FIG. 1. FIG. 1 illustrates an example of the configuration of the information processing system according to the exemplary embodiment.

The information processing system according to the exemplary embodiment includes an information processing device 10, one or more biological information measuring devices, one or more environmental information measuring devices 14, and one or more pieces of equipment 16. In the example illustrated in FIG. 1, the information processing system includes biological information measuring devices 12A and 12B, but this is merely one example. In the following, the information measuring devices 12A and 12B will be referred to as the "biological information measuring device(s) 12" when it is not necessary to distinguish between the information measuring devices 12A and 12B. Note that the number of each type of device illustrated in FIG. 1 is merely one example, and the number of each type of device is not limited to the numbers of devices illustrated in FIG. 1. In addition, the information processing system may also include other devices (for example, an external device such as a server) besides the devices illustrated in FIG. 1.

The information processing device 10, the information measuring device(s) 12, the environmental information measuring device(s) 14, and the equipment 16 are configured to communicate with other devices and the like. The communication may be wired communication using a cable, or wireless communication. In other words, each device may transmit and receive information with each other through physical connection to other devices and the like using a cable, or transmit and receive information with each other through wireless communication. For the wireless communication, a technology such as short-range wireless communication or Wi-Fi (registered trademark) may be used, for example. Wireless communication according to a standard other than the above may also be used. The short-range wireless communication may be a technology such as Bluetooth (registered trademark), radio-frequency identifier (RFID), or NFC, for example. Each device may also communicate with another device, another sensor, or the like through a communication channel such as a local area network (LAN) or the Internet.

The information processing device 10 is for example a personal computer (hereinafter referred to as "PC"), a tablet PC, a smartphone, a mobile phone, or some other type of device. The information processing device 10 may be a terminal device that the user is able to carry (such as a tablet PC, a smartphone, or a mobile phone, for example), or a device that is installed on a table or the like and used. The information processing device 10 may also be a smart speaker including communication functions, a microphone, and a speaker. The information processing device 10 may be installed indoors (such as on the floor, ceiling, or on a table in a room, for example), or may installed outdoors. Additionally, the information processing device 10 may also be a device capable of movement (for example, a self-propelled device).

The biological information measuring devices 12 include components such as sensors and electrodes, and are configured to measure biological information about a user. Each biological information measuring device 12 may measure a different type of biological information. Obviously, some or all of the information measuring devices 12 may also be configured to measure the same type of biological information. In addition, each biological information measuring device 12 may be configured to measure a single type of biological information or multiple types of biological information.

Each biological information measuring device 12 transmits biological information measured by itself to the information processing device 10. Each biological information measuring device 12 may transmit the information to the information processing device 10 every time the information is measured, or each biological information measuring device 12 may store the biological information and transmit the information to the information processing device 10 at predetermined time intervals or transmit the information to the information processing device 10 at a timing specified by the user. Also, each biological information measuring device 12 may receive biological information measured by another biological information measuring device 12 from the other biological information measuring device 12, and transmit the information measured by itself together with the information measured by the other biological information measuring device 12 to the information processing device 10.

Each biological information measuring device 12 may also analyze the information measured by itself or another biological information measuring device, and transmit information indicating the analysis result to the information processing device 10. For example, each biological information measuring device 12 may include a processor, and the process may analyze the information. Obviously, such analysis may also be performed by the information processing device 10.

The biological information measuring device 12 may include a battery and be driven by power supplied from the battery, or be driven by receiving a supply of power from the information processing device 10.

The biological information measuring device 12 may also be a wearable device that is entirely worn on the user and measures biological information. For example, the biological information measuring device 12 may be a device worn on the user's head, a bearable device worn on the user's ear, a device worn on a part of the body such as the user's arm, hand, wrist, or finger (such as a wristwatch-style device for example), a device worn around the user's neck, or a device worn on a part of the body such as the user's torso or leg.

The biological information is any of various types of physiological information and anatomical information produced by the living body of the user. As a conceptual category, biological information includes information such as information indicating the activity of the brain (such as brain waves, the quantity of cerebral blood flow, or a cerebral magnetic field signal, for example), pulse frequency, blood pressure, heart rate, an electrocardiogram waveform, a myoelectric waveform, eye movement, body temperature, perspiration, line of sight, speech, and user movement, for example. The above biological information is merely an example, and other physiological information and anatomical information may also be used as the information. The biological information measuring device 12 may measure one type or multiple types of biological information from among the above types of biological information.

Additionally, the conceptual category of biological information includes bioelectric potential information indicating an electric potential measured from a living body. As a conceptual category, bioelectric potential information includes information such as brain waves obtained as a result of measuring tiny electric currents produced in association with brain activity, an electrocardiogram obtained as a result of measuring tiny electric currents produced in association with the pumping action of the heart, an electromyogram obtained as a result of measuring tiny electric currents produced in association with muscle activity, and electrodermal activity obtained as a result of measuring tiny electric currents occurring in the skin, for example. The above bioelectric potential information is merely an example, and bioelectric potential information other than the above may also be used.

The information processing device 10 receives biological information from the information measuring device 12 and performs operations such as analyzing the information, storing the information, outputting the information, storing information indicating a result of analyzing the information, and outputting information indicating a result of analyzing the information. Obviously, the analysis of the information may also be performed by the information measuring device 12. Outputting the information means displaying the biological information or outputting the information as sound information, for example. Outputting information indicating a result of analyzing the information means displaying information indicating an analysis result or outputting an analysis result as sound information, for example. The information processing device 10 may also transmit information indicating the information and the analysis result to another device.

The information processing device 10 may include one or multiple biological information measuring devices 12. In other words, one or multiple biological information measuring devices 12 may be incorporated into the information processing device 10 to form a single device. The entirety of the information processing device 10 including the one or more biological information measuring devices 12 may also be worn on the user and measure biological information. In other words, the information processing device 10 may also be a wearable device. For example, the information processing device 10 may be a device worn on the user's head, a bearable device worn on the user's ear, a device worn on a part of the body such as the user's arm, hand, wrist, or finger (such as a wristwatch-style device), a device worn around the user's neck, or a device worn on a part of the body such as the user's torso or leg.

The information processing device 10 and the information measuring device 12 may also be separate devices. For example, the information processing device 10 may be a smart speaker, and the information measuring device 12 may be a wearable device worn on the user.

The environmental information measuring device 14 is configured to measure environmental information related to the environment surrounding the user and the environmental information measuring device 14. For example, the environmental information measuring device 14 is a device such as a camera that takes images, a microphone that collects sound, a temperature sensor that measures temperature, a humidity sensor that measures humidity, an odor sensor that measures odors, an illuminance sensor that measures brightness, an infrared sensor, or a presence sensor. One or more of the above sensors may be included in the information processing system as the environmental information measuring device 14.

For example, an image of the surroundings of the information processing apparatus 10 or another place is taken by a camera, and image data expressing the surroundings or image data expressing the other place is generated. The image data may be moving image data or still image data. Image data taken by the camera corresponds to one example of environmental information related to the environment included in the image-taking range of the camera. Also, image data expressing the user that is generated by taking an image of the user with the camera corresponds to one example of biological information about the user. For example, characteristics such as user motion or the user's body type detected from the image data corresponds to one example of biological information about the user. In this sense, the camera corresponds to one example of the biological information measuring device 12 that measures biological information about the user.

Also, sounds around a microphone (for example, a person's speech and other sounds) are input into the microphone, and sound data is generated by the microphone. Sound data expressing the sound input into the microphone corresponds to one example of environmental information related to the environment surrounding the microphone. Also, sound data expressing the user's speech input into the microphone corresponds to one example of biological information about the user. In this sense, the microphone corresponds to one example of the information measuring device 12 that measures biological information about the user.

Likewise, data measured by sensors such as a temperature sensor, a humidity sensor, an odor sensor, an illuminance sensor, an infrared sensor, and a presence sensor corresponds to one example of environmental information. Also, data measured from the user by the above sensors corresponds to one example of biological information about the user. In this sense, the above sensors correspond to one example of the information measuring device 12 that measures biological information about the user.

The environmental information may also include information such as information indicating the size of the room where the user is present, information indicating the size of the room where the equipment is installed, and information indicating the number of windows provided in the room.

Note that one or multiple environmental information measuring devices 14 may be included in the information processing device 10.

The equipment 16 is a device such as a PC, a tablet PC, a smartphone, a mobile phone, a robot (such as a humanoid robot, a non-humanoid animal robot, a cleaning robot, or some other type of robot, for example), a projector, a display device such as a liquid crystal display, a recording device, a playback device, an imaging device such as a camera, a refrigerator, a rice cooker, a microwave oven, a coffee maker, a vacuum cleaner, a washing machine, an air conditioner, lighting equipment, a clock, a surveillance camera, an automobile, a motorcycle, an aircraft (such as an unmanned aerial vehicle (for example, a drone)), a game console, a gas stove, a toilet seat with a bidet function, a ventilation fan, a doorbell, an entrance monitor, an elevator, a door, a window, or any of various types of sensing equipment (such as a temperature sensor, a humidity sensor, a voltage sensor, or a current sensor), for example. Equipment in general may also be included in the conceptual category of the equipment 16. For example, information equipment, video equipment, audio equipment, and other types of equipment may be included in the category of the equipment 16 according to the exemplary embodiment.

The equipment 16 includes a communication device that acts as a communication interface, a storage device that stores data, and a processor that controls the operation of the equipment 16. The equipment 16 may also include a user interface. The equipment 16 may also transmit equipment identification information for identifying the equipment 16 itself to the information processing device 10. For example, the equipment identification information is information such as an ID, a name, a serial number, or an address (such as a MAC address or an IP address for example) of the equipment 16.

Hereinafter, FIG. 2 will be referenced to describe the configuration of the information processing device 10 in detail. FIG. 2 illustrates an example of the configuration of the information processing device 10.

The information processing device 10 includes a communication device 18, a UI 20, a storage device 22, and a processor 24, for example. The information processing device 10 may also include components other than the above.

The communication device 18 is a communication interface, and has a function of transmitting data to other devices and a function of receiving data transmitted from other devices. The communication device 18 may have a wireless communication function, and may also have a wired communication function. The communication device 18 may communicate with another device by using short-range wireless communication for example, or communicate with another device through a communication channel such as a LAN or the Internet. For example, the communication device 18 receives biological information transmitted from the biological information measuring device 12. The communication device 18 may also transmit control information for controlling the operation of the information measuring device 12 to the information measuring device 12. In addition, the communication device 18 receives environmental information transmitted from the environmental information measuring device 14. The communication device 18 may also transmit control information for controlling the operation of the environmental information measuring device 14 to the environmental information measuring device 14. In addition, the communication device 18 transmits control information for controlling the operation of the equipment 16 to the equipment 16. The communication device 18 may also receive information transmitted from the equipment 16.

The UI 20 is a user interface, and includes a display device and an operation device. The display device is a device such as a liquid crystal display or an EL display. The operation device is a device such as a keyboard, input keys, or a control panel. The UI 20 may be a UI such as a touch panel combining a display device with an operation device. In addition, a microphone may also be included in the UI 20, and a speaker that emits sound may also be included in the UI 20.

The storage device 22 is a device that establishes one or multiple storage areas that store various types of data. For example, the storage device 22 is a hard disk drive, any of various types of memory (such as RAM, DRAM, and ROM, for example), another type of storage device (such as an optical disc, for example), or a combination of the above. One or more storage devices 22 are included in the information processing device 10.

Management information is stored in the storage device 22. The management information is information for specifying an operation item of the equipment 16 on the basis of the information measured from the user. For example, predetermined standard biological information and operation information indicating an operation item of the equipment 16 are associated with each other and registered in the management information in advance. The standard biological information may be biological information that is anticipated to occur in the user who performs an operation associated with the standard biological information, or biological information that is anticipated to occur in the user who requests the execution of the operation. The standard biological information may also be considered to be biological information corresponding to an operation item of the equipment 16. The standard biological information and the operation information may be associated with each other and registered in the management information for each user.

In the management information, operation information related to an operation item regarding a power state of the equipment 16 may be registered, operation information related to an operation item regarding a function level of the equipment 16 may be registered, or both operation information related to an operation item regarding the power and operation information related to an operation item regarding a function level may be registered.

The operation item regarding the power state of the equipment 16 is an operation of turning the equipment 16 on or off. The operation information related to the operation item regarding the power state is information indicating an operation of turning the equipment 16 on or off. The biological information associated with the operation information related to the operation item regarding the power state may be considered to be biological information corresponding to turning the equipment 16 on or off. Operation information related to the operation item regarding the power state of the equipment 16 and standard biological information may be associated with each other and registered in the management information for each user.

The operation item regarding a function level of the equipment 16 is an operation of setting a function level of the equipment 16. The operation information related to the operation item regarding a function level is information indicating an operation of setting a function level of the equipment 16. The biological information associated with the operation information related to the operation item regarding a function level may be considered to be biological information corresponding to a function level of the equipment 16. Operation information related to the operation item regarding a function level of the equipment 16 and standard biological information may be associated with each other and registered in the management information for each user.

A function level is a level related to the performance or output of the equipment 16, for example. To give specific examples, the set temperature of an air conditioner, the amount of airflow of an air conditioner, the direction of airflow of an air conditioner, the activation or deactivation of a dehumidifier function of an air conditioner, the brightness of a display device, the brightness of a lighting device, the volume of a speaker, the movement speed of a self-propelled device (such as a robot or a self-propelled vacuum cleaner, for example), settings in devices such as an imaging device, a recording device, and a playback device, settings in devices such as a refrigerator, a rice cooker, and a microwave oven, settings in any of various types of sensing equipment, and the like correspond to examples of function levels. However, the above are merely an example, and set values and the like other than the above may also be function levels.

The processor 24 is configured to acquire biological information about the user and output an instruction for operating the equipment 16 in accordance with the information.

For example, when biological information from the user is measured by the information measuring device 12, the information is transmitted from the biological information measuring device 12 to the information processing device 10. The processor 24 receives the information and ascertains an operation item of the equipment 16 on the basis of the information. The processor 24 operates the equipment 16 by transmitting control information including operation information indicating the ascertained operation item to the equipment 16. The equipment 16 receiving the control information operates in accordance with the control information.

For example, the processor 24 compares biological information measured from the user to each piece of standard biological information registered in the management information above, and searches for standard biological information whose difference from the information is inside a tolerance. The processor 24 specifies the operation item of the equipment 16 associated with the standard biological information returned by the search. With this arrangement, the equipment 16 to be operated is ascertained, and the operation item of the equipment 16 is ascertained. The tolerance is predetermined. The tolerance may also be changed by the user. The tolerance may also be determined for each user.

In the case where the search returns multiple pieces of standard biological information whose difference from the biological information measured from the user is inside the tolerance, the processor 24 specifies the standard biological information having the smallest difference from the information from among the multiple pieces of standard biological information. The processor 24 specifies the operation item of the equipment 16 associated with the specified standard biological information.

The standard biological information may be information indicating a characteristic component of the information. In this case, the processor 24 may extract the characteristic component from the information measured from the user, and search for standard biological information having a component whose difference from the extracted component is inside a tolerance. For example, in the case where brain waves are used as the information, the processor 24 may estimate the operation item expressed by brain waves by extracting a characteristic component from measured brain waves, and analyzing the component.

For example, a brain-machine interface may be constructed by a biological information measuring device 12 that measures the activity of the brain and the information processing device 10. The brain-machine interface may be invasive or non-invasive. In this case, the processor 24 operates the equipment 16 on the basis of the activity (such as brain waves for example) of the user's brain. To operate the equipment 16, the processor 24 may extract a characteristic component from brain waves, and operate the equipment 16 on the basis of the extracted component. To extract a characteristic component from brain waves, techniques such as a fast Fourier transform (FFT), a wavelet transform (WT), a time-frequency distribution (TFD), eigenvector methods (EM), or an autoregressive model (ARM) may be used. Also, as a method of linking brain waves to an operation item of the equipment 16 using feature vectors obtained by feature extraction, for example, techniques such as independent component analysis (ICA), k-means clustering, a support vector machine (SVM), or a convolutional neural network may be used.

In addition, the processor 24 may also be configured to receive equipment identification information transmitted from the equipment 16 and identify the equipment 16. For example, the processor 24 may transmit an acquisition request for equipment identification information to the equipment 16, and acquire equipment identification information transmitted from the equipment 16 in response to the acquisition request. Also, equipment identification information may be transmitted to the information processing device 10 from the equipment 16 made capable of communicating with the information processing device 10 by being connected to the information processing device 10 or the like, and the processor 24 may receive the equipment identification information transmitted in this way.

In addition, the processor 24 may also be configured to control the operation of each unit of the information processing device 10. The processor 24 may include memory.

Also, in the case where biological information about the user satisfying a specific condition is acquired, but a single operation item of the equipment 16 to associate with the acquired biological information is not specified, the processor 24 may query the user about which operation item is to be executed by the equipment 16. The processor 24 associates operation information indicating the operation item designated by the user in response to the query with the acquired biological information, and registers the association in the above management information. The biological information is registered as standard biological information. For example, for each user, the processor 24 associates operation information indicating an operation item designated by a user with biological information measured from the user, and registers the association in the above management information. The biological information is registered as standard biological information about the user.

For example, in the case where standard biological information whose difference from biological information measured from the user is inside a tolerance is not registered in the above management information, the processor 24 queries the user about which operation item is to be executed by the equipment 16.

The processor 24 may cause a query message to be displayed on the UI 20, or cause the message to be output as sound. the processor 24 may query the user about the operation item without specifying an operation item, such as by asking "What is it?", or query the user about the operation item by specifying an operation item, such as by asking "Operation α?".

The user receiving the query may input operation information indicating an operation item into the information processing device 10 by speech, or the user may operate the UI 20 to input operation information indicating an operation item into the information processing device 10. The processor 24 receives the operation information input by the user, associates the operation information with biological information measured from the user, and registers the association in the above management information.

If this usage of associating biological information measured from the user as standard biological information with operation information input by the user is continued, multiple pieces of standard biological information may become associated with a single piece of operation information, and one or multiple pieces of standard biological information may become associated with multiple pieces of operation information.

In the case where multiple pieces of standard biological information are associated with operation information, the multiple pieces of standard biological information may be the same type of biological information or different types of biological information. For example, among the multiple pieces of standard biological information, one piece of the standard biological information may be information indicating brain waves, while another piece of the standard biological information may be information indicating body temperature. In other words, information indicating standard brain waves treated as brain waves expressing an operation item indicated by a piece of operation information and information indicating a standard body temperature treated as a body temperature expressing the operation item may be associated with the operation information. In this case, if brain waves whose difference from the standard brain waves is inside a tolerance are measured from the user, the processor 24 specifies the operation item associated with the standard brain waves, and transmits control information including operation information indicating the operation item to the equipment 16. Also, if a body temperature whose difference from the standard body temperature is inside a tolerance is measured from the user, the processor 24 specifies the operation item associated with the standard body temperature, and transmits control information including operation information indicating the operation item to the equipment 16. As another example, if a brain wave whose difference from the standard brain wave is inside a tolerance and a body temperature whose difference from the standard body temperature is inside a tolerance are measured from the user, the processor 24 may specify the operation item associated with the standard brain wave and the standard body temperature, and transmit control information including operation information indicating the operation item to the equipment 16. Brain waves and body temperature are merely one example of the information, and other biological information may also be associated as standard biological information with operation information.

For example, if the user becomes accustomed to operating the equipment 16 using biological information, the user may conceivably attempt to operate the equipment 16 by producing biological information whose difference from the standard biological information preregistered in the management information is not inside the tolerance. In other words, depending on factors such as the user's familiarity and conditions of use, the information produced from the user when the user intends to operate the equipment 16 may change gradually, and standard biological information whose difference from the changed biological information is inside the tolerance may conceivably not be registered in the management information. In this case, the processor 24 queries the user about the operation item, and associates operation information indicating the operation item designated by the user in response to the query with biological information measured from the user as standard biological information. With this arrangement, even in the case where standard biological information whose difference from biological information measured from the user is inside a tolerance is not registered in the management information, from the next measurement onward, when the information is measured, the equipment 16 may be operated in accordance with the information.

For example, the above biological information satisfying a specific condition is biological information that is not removed by predetermined filtering. Biological information that is removed by filtering is processed as noise, for example. Biological information not removed by filtering has the possibility of being biological information that expresses an operation item. Consequently, in the case where standard biological information whose difference from the information is inside a tolerance is not registered in the management information, the processor 24 queries the user about the operation item. For example, in the case where the information is expressed by a waveform, biological information having an amplitude equal to or greater than a threshold is the biological information satisfying a specific condition. To give a specific example, in the case where the amplitude of a brain wave (for example, a brain wave in a specific frequency band) is equal to or greater than a threshold, the brain wave is the information satisfying a specific condition.

As another example, the above biological information satisfying a specific condition is biological information measured from the user within a predetermined amount of time from a point in time when specific information treated as a trigger is measured from the user. The predetermined amount of time may be changed by the user. Hereinafter, the biospecific information treated as a trigger is referred to as "trigger information". The trigger information is information that is expected to be measured from the user at a point in time before biological information expressing an operation item is measured. For example, the trigger information is information such as specific speech or a specific brain wave indicating that the user is about to produce biological information expressing an operation item. Specific biological information other than the above may also be used as the trigger information. In addition, biological information expressing a state or emotion of the user, such as stress or discomfort, may also be used as the trigger information. For example, because biological information expressing an operation item of the equipment 16 is sometimes measured from the user after biological information expressing stress, discomfort, or the like is measured from the user, the expressing stress, discomfort, or the like may be used as the trigger information. In the case where standard biological information whose difference from biological information measured within a predetermined amount of time from the point in time when the trigger information is measured is inside the tolerance is not registered in the management information, the processor 24 queries the user about the operation item.

In addition, the above biological information satisfying a specific condition may be biological information that is measured within a predetermined amount of time from the point in time when the trigger information is measured, and is not filtered by predetermined filtering. In the case where standard biological information whose difference from the information is inside a tolerance is not registered in the management information, the processor 24 may query the user about the operation item.

As yet another example, the above biological information satisfying a specific condition is biological information measured from the user after an operation is performed on the same equipment 16 a predetermined number of times or more. The biological information measured from the user after an operation is performed on the same equipment 16 a predetermined number of times or more may be biological information first measured from the user after an operation is performed on the same equipment 16 a predetermined number of times or more, or biological information measured from the user within a predetermined amount of time from the point in time when an operation is performed on the same equipment 16 a predetermined number of times or more. The predetermined number of times may be changed by the user. For example, the processor 24 compares biological information measured from the user after an operation is performed on the same equipment 16 a predetermined number of times or more to each piece of standard biological information associated with operation information indicating an operation item of the equipment 16. In the case where standard biological information whose difference from the biological information is inside a tolerance is not registered in the management information, the processor 24 queries the user about the operation item.

Also, the above biological information satisfying a specific condition may be biological information that is measured after an operation is performed on the same equipment 16 a predetermined number of times or more, and is not removed by predetermined filtering.

As yet another example, the above biological information satisfying a specific condition is biological information measured after a predetermined amount of time elapses from a specific point in time. The specific point in time is for example the point in time when the measurement of biological information from the user is started, the point in time when the information measuring device 12 is powered on, the point in time when the equipment 16 is powered on, the point in time when a user account is registered in the information processing device 10 or the equipment 16, or the point in time when the equipment 16 is first operated. The biological information may be biological information first measured from the user after the predetermined amount of time elapses, or biological information measured from the user within a different predetermined amount of time from the point in time when the predetermined amount of time elapses. The predetermined amount of time may be changed by the user.

In the case of querying the user about an operation item, the processor 24 may query the user about an operation item associated with standard biological information having a feature closest to a feature of biological information measured from the user. For example, the standard biological information having a feature closest to a feature of biological information measured from the user is the standard biological information having the highest similarity with the information measured from the user. Note that although the standard biological information is the standard biological information having the highest similarity with the information measured from the user, the difference from the information measured from the user is not inside the tolerance.

In the case where the user does not designate an operation item in response to a query, the processor 24 does not associate operation information indicating an operation item with the information measured from the user. In this case, the information measured from the user is not registered in the management information. For example, in the case where the user does not designate an operation item within a predetermined amount of time from the point in time when the processor 24 queries the user about the operation item, the processor 24 does not associate operation information with the information measured from the user.

In the case where different standard biological information is already registered in the management information in association with operation information indicating the operation item designated by the user in response to the query, the processor 24 may associate the biological information measured from the user instead of the different standard biological information with the operation information. For example, suppose that in the case where standard biological information A1 measured from the user is inside the tolerance is not registered in the management information, standard biological information A2 is already registered in the management information in association with operation information indicating an operation item α specified by the user. In this case, the processor 24 associates the information A1 instead of the standard biological information A2 as new standard biological information with the operation information indicating the operation item α. As a different example, the processor 24 may associate the information A1 together with the standard biological information A2 as new standard biological information with the operation information indicating the operation item α. In this case, the standard biological information A1 and A2 are associated with the operation information indicating the operation item α. In the case where biological information whose difference from the standard biological information A1 is inside the tolerance or biological information whose difference from the standard biological information A2 is inside the tolerance is measured from the user, the processor 24 transmits control information including operation information indicating the operation item α to the equipment 16.

Note that if this usage of associating biological information measured from the user as standard biological information with operation information input by the user in response to a query is continued, multiple pieces of operation information may become associated with a single piece of standard biological information. For example, if this usage is continued, standard biological information registered in the management information in association with a certain operation item α may conceivably be changed to the biological information A1, A2, A3, . . . , An one after another over time. Additionally, the information An associated with the operation item α may conceivably also be associated with a different operation item β. In this case, the processor 24 may query the user about the information associated with multiple pieces of operation information, and ask which of the multiple pieces of operation information is to be associated with the biological information. In the above example, the processor 24 queries the user about whether to associate the biological information An with the operation item α or the operation item β. For example, in the case where the user designates the operation item α as the target of association with the information An, the processor 24 associates the information An as standard biological information with operation information indicating the operation item α, and does not associate the information An with operation information indicating the operation item β.

Also, in the case where the tolerance of the standard biological information A1 associated with the operation item α overlaps with the tolerance of the standard biological information A2 associated with the operation item β, and biological information A3 inside the overlapping tolerance is measured from the user, a single operation item to be associated with the information A3 may not be specified. In this case, the processor 24 may query the user about the operation item to associate with the biological information A3. For example, it is conceivable that, through continued usage according to the exemplary embodiment, the standard biological information associated with the operation item α is gradually changed such that the tolerance of the standard biological information A1 that has come to be associated with the operation item α overlaps with the tolerance of the standard biological information A2 associated with the operation item β. A similar situation may also conceivably occur in the case where the standard biological information associated with the operation item β is changed. In this case, the processor 24 queries the user about whether to associate the information A3 measured from the user with the operation item α or the operation item β. In the case where the user designates the operation item α as the target of association with the biological information A3, the processor 24 associates the biological information A3 as standard biological information with operation information indicating the operation item α, and does not associate the information A3 with operation information indicating the operation item β.

In the case where biological information satisfying a specific condition is measured from the user in a specific environment related to the information satisfying a specific condition, if a single operation item of the equipment 16 to associate with the information is not specified, the processor 24 may query the user about which operation item is to be executed by the equipment 16.

The specific environment is an environment in which operation information indicating an operation item of the equipment 16 is expected to be measured. Under such a specific environment, in the case where biological information satisfying a specific condition is measured but a single operation item to associate with the information is not specified, the processor 24 queries the user about the operation item. The specific environment may be the environment where the user is present, or the user him- or herself, for example. To give specific examples, the specific environment may be properties such as the temperature, humidity, air pressure, or airflow of a room where the user is present, the size of the room, the number of windows installed in the room, brightness, sound volume, odor, the user's body temperature, the user's blood pressure, the amount of movement by the user, or the amount of perspiration by the user. Environmental information indicating the specific environment may be measured by the environmental information measuring device 14 or measured by the information measuring device 12. For example, in the case where the user's body temperature is a threshold or higher, and a single operation item to associate with the biological information measured from the user is not specified, the processor 24 queries the user about an operation item, such as by asking "Do you want to lower the set temperature of the cooler?" As another example, in the case where the information measured from the user is biological information that is similar to standard biological information associated with an operation item that lowers the set temperature of the cooler, the processor 24 may query the user about the operation item, such as by asking "Do you want to lower the set temperature of the cooler?"

Hereinafter, FIG. 3 will be referenced to describe a flow of processes by the information processing device 10. FIG. 3 illustrates a flowchart illustrating a flow of processes by the information processing device 10.

Biological information about the user is measured by the information measuring device 12. The biological information measured by the information measuring device 12 is transmitted to the information processing device 10, and the processor 24 acquires the information (S01). Note that environmental information may also be measured by the environmental information measuring device 14. The environmental information measured by the environmental information measuring device 14 is transmitted to the information processing device 10, and the processor 24 acquires the environmental information.

Next, in the case where the information acquired in step S01 is biological information satisfying a specific condition, the processor 24 compares the information to each piece of standard biological information registered in the management information (S02). On the basis of the comparison, the processor 24 determines whether or not a single operation item to associate with the biological information acquired in step S01 is specified.

For example, in the case where a single piece of standard biological information whose difference from the biological information acquired in step S01 is inside the tolerance is registered in the management information, a single operation item to associate with the information is specified (S03, Yes). In this case, the processor 24 decides the operation item indicated by the operation information registered in the management information in association with the standard biological information as the operation item of the equipment 16 (S04).

Next, the processor 24 transmits control information including operation information indicating the operation item decided in step S04 to the equipment 16 (S05). The equipment 16 receiving the control information operates in accordance with the control information. With this arrangement, the processor 24 operates the equipment 16.

In the case where standard biological information whose difference from the information acquired in step S01 is inside the tolerance is not registered in the management information, a single operation item to associate with the information is not specified (S03, No). In this case, the processor 24 queries the user about the operation item to be executed by the equipment 16 (S06).

Also, in the case where multiple pieces of standard biological information whose difference from the information acquired in step S01 is inside the tolerance are registered in the management information, a single operation item to associate with the information is not specified (S03, No). In this case, the processor 24 queries the user about the operation item to be executed by the equipment 16 (S06). Note that the processor 24 may also query the user about an operation item associated with standard biological information having a feature closest to a feature of biological information measured from the user.

In the case where the user designates an operation item in response to a query, the processor 24 registers the biological information acquired in step S01 and operation information indicating the operation item in association with each other in the management information (S07). The biological information is associated as standard biological information with the operation information.

Subsequently, the process returns to step S04. The processor 24 decides the operation item designated by the user as the operation item of the equipment 16 (S04), and transmits control information including operation information indicating the operation item to the equipment 16 (S05).

Hereinafter, a specific example of the management information will be described.

FIG. 4 illustrates an example of a management table as one example of the management information. The data in the management table is stored in the storage device 22. The data in the management table may also be stored in an external device such as a server, without being stored in the storage device 22.

In the management table, an ID, a standard brain wave, an operation information indicating an operation item of the equipment 16 are associated with each other in advance. The standard brain wave is one example of standard biological information. Herein, a brain wave is used as one example of the standard biological information, but biological information other than brain waves may also be used as the standard biological information.

The ID is information for managing the information registered in the management table.

The standard brain wave is determined by statistical processing, for example, and is a brain wave that is generally anticipated to be occur in the user who performs the operation item associated with the standard brain wave, or a brain wave that is generally anticipated to occur in the user who requests the execution of the operation item.

The standard brain wave may be a brain wave in a specific frequency band, or a brain wave containing brain waves in multiple frequency bands.

The operation information is information including equipment identification information for identifying the equipment 16 to be operated and information indicating the operation item to be performed with respect to the equipment 16. For example, the operation item may be an operation of turning the equipment 16 on or off, or an operation of setting a function level of the equipment 16.

For example, the standard brain wave with the ID "1" is a brain wave expressing an operation item of turning on the cooler of an air conditioner. The standard brain wave with the ID "2" is a brain wave expressing an operation item of turning off the cooler of an air conditioner.

For example, in the case where a brain wave whose difference from the standard brain wave with the ID "1" is inside the tolerance is measured from the user, the processor 24 specifies the operation item of "turn on cooler of air conditioner" associated with the standard brain wave. Additionally, the processor 24 transmits control information including information indicating the operation item of "turn on cooler of air conditioner" to the air conditioner. The air conditioner operates in accordance with the control information. With this arrangement, the cooler of the air conditioner turns on.

Also, the processor 24 may compute a similarity between a brain wave measured from the user and a standard brain wave, and determine whether or not the similarity is a threshold or greater. The threshold is a value corresponding to the tolerance. In the case where the similarity between the brain wave measured from the user and the standard brain wave is the threshold or greater, the processor 24 determines that the brain wave measured from the user and the standard brain wave are similar to each other. In other words, the processor 24 determines that the difference between the brain wave measured from the user and the standard brain wave is inside the tolerance. In the case where a brain wave whose similarity with the standard brain wave with the ID "1" is the threshold or greater is measured from the user, the processor 24 specifies the operation item of "turn on cooler of air conditioner".

The standard biological information and the operation information may be associated with each other and registered in the management table for each user. For example, biological information measured from a user may be registered as standard biological information for the user in the management table.

FIG. 5 illustrates an example of a management table in which specific standard biological information for individual users is registered. In the management table illustrated in FIG. 5, an ID, a standard brain wave given as an example of standard biological information, operation information, and user information are associated with each other.

The user information is information for identifying each user (such as a username or a user ID, for example).

The standard brain wave associated with the user information is a brain wave measured from the user when the user indicated by the user information performs the operation item associated with the standard brain wave, or a brain wave measured from the user when the user requests the operation item. Each standard brain wave measured from each user is measured from each user in advance and registered in the management table.

For example, the brain wave of a user A when the user A manually turns on the cooler of the "air conditioner" is measured by the information measuring device 12, and the measured brain wave is registered in the management table as a standard brain wave expressing the operation item of "turn on cooler of air conditioner" by the user A.

In this case, the measured standard brain wave of the user A is registered in the management table in association with operation information indicating the operation item of "turn on cooler of air conditioner" and user information for identifying the user A. The registration may be performed using the information processing device 10 or using another device. In the example illustrated in FIG. 5, the information is registered as the information with the ID "1". The same applies to other operations and other users.

Note that the work of registration may also be performed multiple times, and the average of multiple brain waves measured thereby may also be registered as a standard brain wave. For example, the work of the user manually turning on the cooler of the "air conditioner" and the biological information measuring device 12 measuring the brain wave produced from the user A at the time may be performed multiple times, and an average of the multiple brain waves measured thereby may be registered in the management table as a standard brain wave of the user A.

For example, in the case where the user A is logged in to the information processing device 10, and a brain wave whose difference from the standard brain wave with the ID "1" is inside the tolerance is measured from the user A, the processor 24 turns on the cooler of the "air conditioner" by transmitting control information including the operation information corresponding to the ID "1" to the "air conditioner". Described in further detail, if a brain wave is measured by the information measuring device 12 while the user A is logged in to the information processing device 10, the processor 24 searches for a standard brain wave that is registered in the management table in association with user information for identifying the logged-in user A. In the example illustrated in FIG. 5, the standard brain wave with the ID "1" and the standard brain wave with the ID "3" are registered in the management table as standard brain waves of the user A, and therefore these standard brain waves are returned by the search. In the case where the difference between the measured brain wave and the standard brain wave with the ID "1" is inside the tolerance, the processor 24 turns on the cooler of the "air conditioner" by transmitting control information including the operation information corresponding to the ID "1" to the "air conditioner". In the case where the difference between the measured brain wave and the standard brain wave with the ID "3" is inside the tolerance, the processor 24 turns off the cooler of the "air conditioner" by transmitting control information including the operation information corresponding to the ID "3" to the "air conditioner".

As another example, in the case where the user operating the equipment 16 is set to "user A" in the information processing device 10, and a brain wave whose difference from the standard brain wave with the ID "1" is inside the tolerance is measured from the user A, the processor 24 may turn on the cooler of the "air conditioner" by transmitting control information including the operation information corresponding to the ID "1" to the "air conditioner". Described in further detail, if a brain wave is measured by the information measuring device 12 while the user operating the equipment 16 is set to "user A" in the information processing device 10, the processor 24 searches for a standard brain wave that is registered in the management table in association with user information for identifying the user A who is the user operating the equipment 16. In the case where the difference between the measured brain wave and the standard brain wave with the ID "1" is inside the tolerance, the processor 24 turns on the cooler of the "air conditioner" by transmitting control information including the operation information corresponding to the ID "1" to the "air conditioner". The user operating the equipment 16 is set in the information processing device 10 by the user, for example.

For users other than the user A, each piece of information is likewise registered in the management table similarly to the user A. For example, each piece of information associated with the ID "2" is information related to an operation when a user B turns on the cooler of the "air conditioner". Each piece of information associated with the ID "3" is information related to an operation when the user A turns off the cooler of the "air conditioner".

In the management tables illustrated in FIGS. 4 and 5, operation information indicating operations for turning the equipment 16 on or off is registered, but operation information indicating a function level of the equipment 16 may also be registered in the management table.

Figures 6, 7:
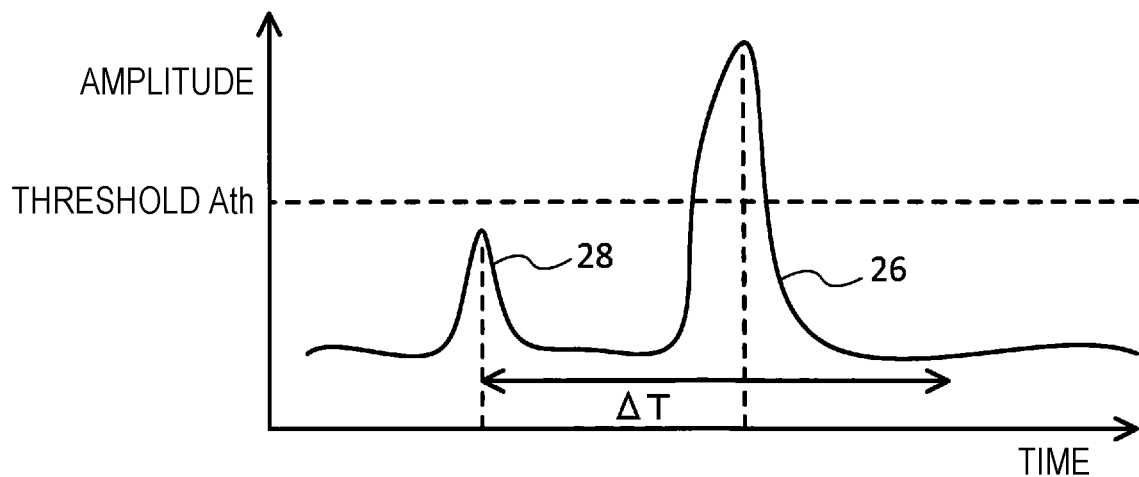
FIG. 6 is a graph illustrating a waveform of biological information.
FIG. 7 is a diagram illustrating a management table.

Hereinafter, FIG. 6 will be referenced to describe biological information satisfying a specific condition in detail. FIG. 6 illustrates an example of a brain wave as one example of biological information. The horizontal axis represents time, while the vertical axis represents the amplitude of the brain wave. Although a brain wave is given here as one example of biological information, biological information other than a brain wave may also be used.

For example, a brain wave satisfying a specific condition is biological information that is not removed by predetermined filtering. Specifically, a brain wave having an amplitude equal to or greater than a threshold Ath is the brain wave satisfying a specific condition. For example, because the peak of a waveform 26 has an amplitude equal to or greater than the threshold Ath, the waveform 26 is the brain wave satisfying a specific condition. In the case where a single operation item of the equipment 16 to associate with the waveform 26 is not specified, the processor 24 queries the user about which operation item is to be executed by the equipment 16. For example, in the case where a standard brain wave whose difference from the waveform 26 is inside the tolerance is not registered in the management table illustrated in FIG. 4, the processor 24 queries the user about the operation item. Also, in the case where the waveform 26 is measured from the user A, and a standard brain wave associated with user information indicating the user A and whose difference from the waveform 26 is inside the tolerance is not registered in the management table illustrated in FIG. 5, the processor 24 queries the user A about the operation item. The same applies to users other than the user A.

As another example, the brain wave satisfying a specific condition is a brain wave measured from the user within a predetermined amount of time ΔT from a point in time when trigger information is measured from the user. For example, a waveform 28 is one example of trigger information. The amount of time ΔT may also be changed by the user. The waveform 28 may be a specific brain wave expressing that the user is about to produce a brain wave expressing an operation item, but may also be a brain wave expressing a state or emotion of the user, such as stress or discomfort. The point in time when the waveform 28 acting as the trigger information is measured may be the point in time when the peak of the waveform 28 is measured or the point in time when a waveform having an amplitude equal to or greater than a predetermined amplitude is measured, for example. The waveform 26 is measured from the user within the amount of time ΔT from the point in time when the waveform 28 is measured. Consequently, the waveform 26 is the brain wave satisfying a specific condition. A brain wave measured within the amount of time ΔT from the point in time when the waveform 28 acting as the trigger information is measured and having an amplitude equal to or greater than the threshold Ath may be the brain wave satisfying a specific condition. For example, the waveform 26 satisfies such a condition.

Hereinafter, FIG. 7 will be referenced to describe a process of associating biological information measured from the user with operation information in detail. Herein, a process of associating biological information and operation information for each user will be described. FIG. 7 illustrates an example of the management table. Like the management table illustrated in FIG. 5, the management table illustrated in FIG. 7 is a management table in which a standard brain wave and operation information are associated with each other and registered for each user.

The information associated with each of the IDs "1" to "3" is the same as the information illustrated in FIG. 5. The information associated with the ID "4" is information newly added to the management table illustrated in FIG. 5. The management table illustrated in FIG. 5 is the management table before the information associated with the ID "4" is registered, while the management table illustrated in FIG. 7 is the management table after the information associated with the ID "4" is newly registered.

Before the information associated with the ID "4" is registered in the management table, the management table illustrated in FIG. 5 is used. In this situation, suppose that the brain wave with the ID "4" is measured from the user A, and the brain wave is the brain wave satisfying a specific condition. In this case, the processor 24 compares the brain wave measured from the user A to each standard brain wave registered in the management table illustrated in FIG. 5 and associated with user information indicating the user A. In the case where a standard brain wave whose difference from the brain wave with the ID "4" is inside the tolerance is not registered in the management table in association with the user information indicating the user A, the processor 24 queries the user A about the operation item. In the case where the user A designates an operation item with the content of "turn off cooler of air conditioner" in response to the query, the processor 24 associates the brain wave measured from the user A as a standard brain wave with operation information indicating the operation item. In addition, the processor 24 associates the standard brain wave and the operation information with user information indicating the user A. Furthermore, as illustrated in FIG. 7, the processor 24 registers the above information in the management table as information associated with the ID "4". With this arrangement, the management table is updated from the management table illustrated in FIG. 5 to the management table illustrated in FIG. 7. Thereafter, the processor 24 uses the management table illustrated in FIG. 7 to specify an operation item on the basis of a brain wave measured from the user.

As illustrated in FIG. 7, the standard brain wave with the ID "3" and the standard brain wave with the ID "4" are associated with user information indicating the user A and operation information indicating the operation item of "turn off cooler of air conditioner". In other words, in the case where a brain wave whose difference from the standard brain wave with the ID "3" is inside the tolerance or a brain wave whose difference from the standard brain wave with the ID "4" is inside the tolerance is measured from the user A, the processor 24 specifies the operation item of "turn off cooler of air conditioner" as the operation item of the equipment 16, and transmits operation information indicating the operation item to the air conditioner which is one example of the equipment 16. In this way, multiple standard brain waves may be associated with operation information indicating a single operation item.

FIG. 8 illustrates a different example of the management table. The management table illustrated in FIG. 8 is a management table in which standard biological information and operation information are associated with each other and registered for each user. In the example illustrated in FIG. 8, brain waves and body temperature are used as the standard biological information as an example. Consequently, in the management table, an ID, a standard brain wave given as an example of standard biological information, a standard body temperature given as an example of standard biological information, operation information, and user information are associated with each other.

For example, in the case where a brain wave whose difference from the standard brain wave with the ID "1" is inside the tolerance is measured from the user A, and a body temperature equal to or greater than a threshold is measured from the user A, the processor 24 specifies the operation item indicated by the operation information with the ID "1" as the operation item of the equipment 16.

In the case where at least one of the brain wave and the body temperature measured from the user A satisfies a specific condition, but a single operation item of the equipment 16 is not specified on the basis of the brain wave and the body temperature measured from the user A, the processor 24 queries the user A about the operation item of the equipment 16. The processor 24 registers operation information indicating an operation item designated by the user A in response to the query and the brain wave and the body temperature measured from the user A in association with each other in the management table. The processor 24 also associates user information indicating the user A with the above information. The brain wave is registered as a standard brain wave in the management table, and the body temperature is registered as a standard body temperature in the management table. Note that the standard body temperature may also be a value having a predetermined range set as the standard for the body temperature measured from a user.

FIG. 9 illustrates yet another management table. The management table illustrated in FIG. 9 is a management table in which a standard brain wave, standard environmental information, and operation information are associated with each other and registered for each user. A standard brain wave is used as one example of the standard biological information, but other biological information may also be used as the standard biological information.

The standard environmental information is information indicating an environment in which the standard brain wave associated with the standard environmental information is expected to be measured. Room temperature is used as the standard environmental information, but other environmental information may also be used as the standard environmental information.

For example, in the case where a brain wave whose difference from the standard brain wave with the ID "1" is inside the tolerance is measured from the user A, and the room temperature is 28° C. or greater when the brain wave is measured, the processor 24 specifies the operation item indicated by the operation information with the ID "1" as the operation item of the equipment 16. In this way, an operation item of the equipment 16 is measured on the basis of a brain wave measured from the user and the room temperature when the brain wave is measured.

In the case where a brain wave measured from the user A satisfies a specific condition, but a single operation item of the equipment 16 is not specified on the basis of the brain wave measured from the user A, the processor 24 queries the user A about the operation item of the equipment 16. The processor 24 registers information indicating an operation item designated by the user A in response to the query, the brain wave measured from the user A, the room temperature when the brain wave was measured, and user information indicating the user A in association with each other in the management table. The brain wave is registered as a standard brain wave in the management table, and the room temperature is registered as standard environmental information in the management table. Note that the room temperature indicated by the standard environmental information may also be a value having a predetermined range set as a standard for the room temperature when the brain wave is measured.

Also, in the case where a brain wave measured from the user A satisfies a specific condition and the room temperature is 28° C. when the brain wave is measured, but a single operation item of the equipment 16 is not specified on the basis of the brain wave measured from the user A, the processor 24 may also query the user A about the operation item indicated by the operation information associated with the standard environmental information indicating that the room temperature is 28° C. or greater and the user information indicating the user A. In the example illustrated in FIG. 9, the standard environmental information indicating that the room temperature is 28° C. or greater and the user information indicating the user A are information associated with the ID "1". Consequently, the processor 24 queries the user about the operation item by asking "Do you want to turn on the cooler of the air conditioner?" The user may respond to the query with content such as "Yes" or "No", or designate a specific operation item. For example, in the case where the user answers "Yes", the processor 24 registers a brain wave measured from the user A, the above standard environmental information, operation information indicating the operation item of "turn on cooler of air conditioner", and user information indicating the user A in association with each other in the management table. The brain wave is registered in the management table as a standard brain wave. Also, in the case where the user designates a specific operation item, the processor 24 registers a brain wave measured from the user A, the above standard environmental information, operation information indicating the designated operation item, and user information indicating the user A in association with each other in the management table.

Note that in the exemplary embodiment above, the processing by the processor 24 may also be executed by another device (for example, an external device such as a server) other than the information processing device 10, and information indicating a result of the processing may be displayed on the UI 20 or output as sound information.

In the embodiment above, the term "processor" refers to hardware in a broad sense. Examples of the processor includes general processors (e.g., CPU: Central Processing Unit), dedicated processors (e.g., GPU: Graphics Processing Unit, ASIC: Application Integrated Circuit, FPGA: Field Programmable Gate Array, and programmable logic device).

In the embodiment above, the term "processor" is broad enough to encompass one processor or plural processors in collaboration which are located physically apart from each other but may work cooperatively. The order of operations of the processor is not limited to one described in the embodiment above, and may be changed.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing device comprising:
a processor, wherein in a case in which a user, brain wave information of the user and a single operation item of equipment are associated and recorded as reference information, the processor is configured to
query the user about an operation item to be executed by equipment only in a case where brain wave information about the user satisfying a specific condition is acquired, but the single operation item of equipment to associate with the acquired brain wave information is not specified based on the reference information, and
associate and record an operation item designated by the user in response to the query with the acquired brain wave information and the user, as updated reference information.

2. The information processing device according to claim 1, wherein the brain wave information satisfying the specific condition is brain wave information that is not removed by predetermined filtering.

3. The information processing device according to claim 1, wherein the brain wave information satisfying the specific condition is brain wave information acquired within a predetermined amount of time from a point in time when specific information treated as a trigger is measured from the user.

4. The information processing device according to claim 1, wherein the brain wave information satisfying the specific condition is brain wave information acquired after an operation is performed on the equipment a predetermined number of times or more.

5. The information processing device according to claim 1, wherein in a case where the single operation item of equipment to associate with the acquired brain wave information is not specified, the processor is configured to query the user about an operation item associated with brain wave information having a feature closest to a feature of the acquired brain wave information.

6. The information processing device according to claim 1, wherein
in a case where an operation item is not designated by the user in response to the query, the processor is configured to
not associate an operation item with the acquired brain wave information.

7. The information processing device according to claim 1, wherein
in a case where an operation item designated by the user in response to the query is associated with different biological information, the processor is additionally configured to
associated the acquired brain wave information instead of the different biological information with the operation item designated by the user.

8. The information processing device according to claim 1, wherein in addition to the user, brain wave information of the user and the single operation item of equipment, environmental information is associated and recorded as the reference information, and
only in a case where the brain wave information satisfying the specific condition is acquired, but the single operation item of equipment to associate with the acquired brain wave information and measured environmental information is not specified, the processor is configured to
query the user about an operation item to be executed by the equipment.

9. The information processing device of claim 8, wherein the environmental information includes at least one of image information, sound information, temperature information, humidity information, odor information, brightness information, or infrared information.

10. The information processing device of claim 1, wherein the device is configured to be worn on the user's ear.

11. The information processing device of claim 1, wherein the brain wave information is measured by a brain wave information measuring device that is worn on the user's ear.

12. A non-transitory computer readable medium storing a program causing a computer to execute a process for processing information, the process comprising:
in a case in which a user, brain wave information of the user and a single operation item of equipment are associated and recorded as reference information,
querying the user about an operation item to be executed by equipment only in a case where brain wave information about the user satisfying a specific condition is acquired, but a single operation item of the equipment to associate with the acquired brain wave information is not specified based on the reference information, and
associating and recording an operation item designated by the user in response to the query with the acquired brain wave information and the user, as updated reference information.

13. An information processing device comprising:
a querying means for querying a user about an operation item to be executed by equipment only in a case where brain wave information about the user satisfying a specific condition is acquired, but a single operation item of the equipment to associate with the acquired brain wave information is not specified based on the reference information; and
an associating means for associating and recording an operation item designated by the user in response to the query with the acquired brain wave information and the user, as updated reference information.

14. A method comprising:
in a case in which a user, brain wave information of the user and a single operation item of equipment are associated and recorded as reference information, configuring a processor to:
query the user about an operation item to be executed by equipment only in a case where brain wave information about the user satisfying a specific condition is acquired, but a single operation item of equipment to associate with the acquired brain wave information is not specified based on the reference information, and
associate and record an operation item designated by the user in response to the query with the acquired brain wave information and the user, as updated reference information.

* * * * *